United States Patent [19]
Roorda et al.

[11] Patent Number: 5,571,525
[45] Date of Patent: Nov. 5, 1996

[54] EROSION RATE MODIFIER FOR USE IN BIOERODIBLE DRUG DELIVERY DEVICES AND METHOD OF USE

[75] Inventors: Wouter E. Roorda, Newark; Fred Ehnow, Mountain View, both of Calif.

[73] Assignee: Alza Corporation, Palo Alto, Calif.

[21] Appl. No.: 307,845

[22] PCT Filed: Mar. 30, 1993

[86] PCT No.: PCT/US93/03003

§ 371 Date: Sep. 30, 1994

§ 102(e) Date: Sep. 30, 1994

[87] PCT Pub. No.: WO93/20134

PCT Pub. Date: Oct. 14, 1993

[51] Int. Cl.⁶ .................................................. A61K 9/14
[52] U.S. Cl. ...................... 424/426; 424/422; 424/401; 424/490; 424/494
[58] Field of Search ................................ 424/426, 422, 424/401

[56] References Cited

U.S. PATENT DOCUMENTS

| | | | |
|---|---|---|---|
| 3,991,766 | 11/1976 | Schmitt et al. | 606/230 |
| 4,070,347 | 1/1978 | Schmitt | 528/271 |
| 4,093,709 | 6/1978 | Choi et al. | 424/424 |
| 4,122,158 | 10/1978 | Schmitt | 424/444 |
| 4,131,648 | 12/1978 | Choi et al. | 424/484 |
| 4,138,344 | 2/1979 | Choi et al. | 252/1 |
| 4,155,992 | 5/1979 | Schmitt | 514/772.7 |
| 4,180,646 | 12/1979 | Choi et al. | 528/153 |
| 4,322,323 | 3/1982 | Capozza | 424/426 |
| 4,346,709 | 8/1982 | Schmitt | 424/426 |
| 4,489,056 | 12/1984 | Himmelstein et al. | 424/486 |
| 4,780,320 | 10/1988 | Baker | 424/493 |
| 4,917,892 | 4/1990 | Speaker et al. | 424/401 |
| 4,919,939 | 4/1990 | Baker | 424/493 |
| 4,940,588 | 7/1990 | Sparks et al. | 424/490 |
| 4,962,091 | 10/1990 | Eppstein et al. | 514/2 |
| 5,008,117 | 4/1991 | Calanchi et al. | 424/494 |
| 5,077,049 | 12/1991 | Dunn et al. | 424/422 |
| 5,098,443 | 3/1992 | Parel et al. | 623/4 |
| 5,194,473 | 3/1993 | Shinoda et al. | 524/263 |

FOREIGN PATENT DOCUMENTS

| | | |
|---|---|---|
| 244118 | 4/1987 | European Pat. Off. . |
| 0019226 | 11/1992 | WIPO . |
| 0005265 | 3/1994 | WIPO . |

OTHER PUBLICATIONS

WO,A,9 213 567 (Nova Pharmaceutical Corporation), 20 Aug. 1992.
Journal of Controlled release, vol. 15, No. 1, Feb. 1990, Amsterdam NL, pp. 55–63.
Shih, Lucas, Zeniner; Acid catalyzed poly(ortho ester matrices for intermediate term drug delivery.
Pharmazie, vol. 47, No. 6, 1992, Berlin DD, pp. 436–439, Thoma, Schlutermann, Beziehungen zwischen Herstellungsparametern und pharmazeutisch–technologischen Anforderungen an biodegradierbare Mikropartikel.
J. Heller, Biomaterials, 1990, vol. 11:659–661, "Development of poly (ortho esters): a historical overview".

*Primary Examiner*—Thurman K. Page
*Assistant Examiner*—Sharon Howard
*Attorney, Agent, or Firm*—Mary Ann Dillahunty; Richard T. Ito; Steven F. Stone

[57] ABSTRACT

This invention resides in the field of bioerodible polymers for use as drug delivery vehicles. In particular, this invention addresses means for controlling the rate of biodegradation and degradation in general of such polymers.

10 Claims, 3 Drawing Sheets

EROSION RATE MODIFIER FOR USE IN BIOERODIBLE DRUG DELIVERY DEVICES AND METHOD OF USE

BACKGROUND OF THE INVENTION

One of many known methods of achieving sustained delivery of a drug is by incorporating the drug in a solid polymeric matrix formed from a bioerodible polymer. Formulations of this type are primarily used for parenteral administration. The matrix may assume a variety of forms, but most often is either in the shape of thin rods suitable for injection, or microscopic particles suitable for application as a dry sprinkle or in a suitable liquid vehicle for injection.

The term "bioerodible" refers to the quality of the polymer that causes it to be degraded or eroded in vivo. This occurs either through enzymatic action or other types of action, and decomposes the polymer into biocompatible, non-toxic by-products which are further metabolized or excreted from the body through the normal physiological pathways, without raising an immunological reaction.

Among the wide variety of polymers having this quality, some which are of particular interest in this invention are poly(orthoester)s and poly(orthocarbonate)s. Such bioerodible polymers are disclosed in Schmitt, U.S. Pat. No. 4,070,347, Jan. 24, 1978; Choi, et al., U.S. Pat. No. 4,093,709, Jun. 6, 1978; Schmitt, U.S. Pat. No. 4,122,158, Oct. 24, 1978; Choi, et el., U.S. Pat. No. 4,131,648, Dec. 26, 1978; Choi, et al., U.S. Pat. No. 4,138,344, Feb. 6, 1979; Schmitt, U.S. Pat. No. 4,155,992, May 22, 1979; Choi, et al., U.S. Pat. No. 4,180,646, Dec. 25, 1979; Capozza, U.S. Pat. No. 4,322,323, Mar. 30, 1982; and Schmitt, U.S. Pat. No. 4,346,709, Aug. 31, 1982. The disclosures in these patents are incorporated herein by reference.

Other bioerodible polymers which are of interest in this invention are poly(lacticacid), poly(glycolic acid) and copolymers of lactic acid and glycolic acid. Published literature relevant to these polymers are Schmitt, et al., U.S. Pat. No. 3,991,766, issued Nov. 16, 1976; Yoles, S., et al., *Polymer News* 1(4/5):9–15 (1971); Kulkarni, R. K., et al., *J. Biomed. Mater. Res.* 5:169–181 (1971); and Wise, D. L., *Acta Pharm. Suecica* 13 (suppl.):34 (1976).

In Shih et al., *Journal of Controlled Release* 15:55–63 (Feb. 1990), "Acid Catalyzed poly(orthoester) Matrices for Intermediate Term Drug Delivery," the in vitro release of timolol maleate from poly(orthoester) matrices with lipophilic acid catalysts was studied.

In U.S. Pat. No 4,780,319 carboxylic acids are incorporated into polymers to catalyze the erosion of the polymer matrix. Poly(orthoesters), poly(orthocarbonates), polymers of ketenacetal and polyols, polyacetals, polyketals, polyacetates, polyglycolates and polycaprolactones are listed as the possible polymers.

In U.S. Pat. No. 4,346,709 erodible devices comprising a poly(orthoester) or poly(orthocarbonate), a drug and an erosion rate modifier are disclosed. The erosion rate modifiers can either increase or decrease the rate of erosion.

In these formulations in general, the drug is originally dispersed in and held immobile by the polymeric matrix, and the release of the drug from the matrix occurs gradually over a period of time. This sustained release is achieved by one or a combination of mechanisms, including diffusion of the drug through molecular interstices in the polymer, diffusion of the drug through pores in the polymer (if a pore-forming ingredient has been used in the formation of the polymer), and degradation of the polymer itself. The release rate may be controlled to a certain-degree by varying certain system parameters, such as the size and shape of the polymer systems, the choice of polymer used to form the matrix, the molecular weight and density of the polymer, the ratio of drug to polymer, the pore structure of the matrix, the inclusion of additional components such as erosion rate modifiers in the matrix, and the choice of carrier vehicle where one is used.

Degradation of the polymer is potentially the greatest contributing factor to the release of the drug, since degradation reduces and ultimately removes the diffusion barriers which retard the passage of the drug through the matrix. Also, there are certain drugs which are released from the matrix primarily by erosion or degradation of the polymer and not by diffusion. Theoretically, therefore, the release rate may be regulated either up or down by increasing or decreasing the polymer degradation rate. Attempts to do this in the prior art have involved the inclusion of erosion rate modifiers as additives mixed in with the polymers, the modifiers selected either to promote or to inhibit the degradation reaction. Disclosures of erosion rate modifiers and their use appear in Schmitt, U.S. Pat. No. 4,346,709, Aug. 31, 1982, which discloses metals, metal oxides, metal oxide salts, metal hydroxides, amines, organic and inorganic acids, and monobasic and polybasic acids, and Capozza, U.S. Pat. No. 4,322,323, Mar. 30, 1982, which discloses anionic, cationic and nonionic surfactants.

Modifiers known to the prior art are not always a satisfactory solution, however, since under certain circumstances the modifiers tend to diffuse out of the polymer into the surrounding medium. This causes a sharp drop in the effectiveness of the modifier, and the resulting curve of the release rate of the drug vs. time changes in slope. This is particularly the case with highly water-soluble modifiers. When such a water-soluble modifier is a degradation inhibitor, for example, the desired slow release rate lasts only through the initial stages of the release period and is followed by release at a rate which is faster than desired. Conversely, when such a modifier is a degradation promoter, the desired fast release lasts only initially, leaving a significant quantity of the drug to be released from the polymer matrix at too slow a rate. The loss of effectiveness may be compensated for by using a particularly strong modifier which will continue to work at low concentrations. In systems where the modifier is an acid or base, for example, a strong modifier will be one with a low $pK_a$ or $pK_b$, respectively. High strength modifiers, however, can compromise the stability of acid- or base-sensitive drugs in the polymer system and, depending on the modifier, raise physiological risks and toxicity questions by releasing free quantities of modifier when administered to a patient.

Additionally, prior art modifiers are often not satisfactory due to the fact that they have been incorporated into the polymer in such a way that they are not mixed with the polymer on a molecular level but are present in a separate phase, which is dispersed on a supra-molecular level through the polymer matrix. This leads to a loss of efficiency and to the use of higher strength modifiers. Also, the high strength acid or base modifier, being in a separate phase from the polymer, is available to come into contact with and adversely affect drugs or other agents present in the polymer matrix which are sensitive to the modifier.

The present invention addresses these and other disadvantages and shortcomings of these and other methods of regulating the biodegradation rate of polymer matrices.

SUMMARY OF THE INVENTION

It has now been discovered that the biodegradation rate of bioerodible polymers can be regulated in an unusually efficient manner by the use of erosion rate modifiers whose solubility in the polymer is high relative to their solubility in an aqueous medium. Modifiers in accordance with this invention reside in the matrix as a solute in the solid or semi-solid polymer, on a molecular level, rather than as a separate solid or liquid phase, and have a greater tendency to remain in solution in the polymer than to dissolve in, and diffuse through, the generally aqueous environment in which the polymer is placed for use.

By virtue of this tendency, the modifiers offer several advantages over modifiers of the prior art. First, the modifiers may be selected from milder compounds, for example, such as weaker acids and bases and usually less toxic compounds. This lowers the risk of harm to the physiological systems to which the formulation is being administered, and the risk of undesired chemical attack by the modifiers to the polymer or to the drug which is retained by the polymer for controlled release. Second, the modifiers of the invention permit one to achieve stronger modifications in the degradation rate, since they are in closer proximity to the polymer and remain so during the life of the polymer. Third, the modifiers permit one to achieve substantial and effective results with a lower loading of modifier, which improves the economy of materials used, and requires less interference with and variation of the chemical composition of the formulation.

The invention is of particular interest in its application to bioerodible polymers whose biodegradation rate is regulated by acids or bases. The biodegradation reaction may occur by any of a variety of mechanisms. Hydrolysis is one of the most prominent of these mechanisms, occurring either alone or in conjunction with enzyme action in a biological environment. Depending on the type of polymer involved, the hydrolysis may be accelerated or inhibited by acids, bases, or both.

In particular, the invention relates to a method for treating a bioerodible polymer selected from the group consisting of polymers of copolymers of d,l-lactic and glycolic acids to accelerate the rate of bioerosion thereof, said method comprising incorporating into said bioerodible polymer an additive selected from the group consisting of acids and bases which are soluble in said bioerodible polymer and substantially insoluble in water and have a pK of at least about 2.0, at a concentration at or below the upper solubility limit of said additive in said bioerodible polymer, said additive and said polymer forming a single homogeneous phase.

The invention further relates to a bioerodible polymer matrix system which comprises a bioerodible polymer wherein said polymer is a member selected from the group consisting of copolymers of d,l-lactic and glycolic acids, and an erosion rate modifier selected from an acid or a base which is soluble in said polymer and substantially insoluble in water and has a pK of at least 2.0, said erosion rate modifier being dissolved in said bioerodible polymer at a concentration at or below the upper solubility limit of said erosion rate modifier in said bioerodible polymer, said erosion rate modifier and said polymer forming a single homogeneous phase.

The invention also relates to a delivery device for the controlled administration of a beneficial agent to an environment of use, wherein the device comprises a shaped matrix sized and adapted for administering a drug to an animal, said matrix comprising a bioerodible polymer wherein said polymer is a member selected from the group consisting of copolymers of d,l-lactic and glycolic acids and an erosion rate modifier selected from an acid or a base which is soluble in said polymer and substantially insoluble in water and has a pK of at least 2.0, said erosion rate modifier being dissolved in said bioerodible polymer at a concentration at or below the upper solubility limit of said erosion rate modifier in said bioerodible polymer, said erosion rate modifier and said polymer forming a single homogeneous phase; and the drug to be delivered, dispersed in said matrix in a therapeutically effective amount.

Further features, embodiments, applications and advantages of the invention will become apparent from the description which follows.

DETAILED DESCRIPTION OF THE INVENTION AND PREFERRED EMBODIMENTS

Figure 1A:
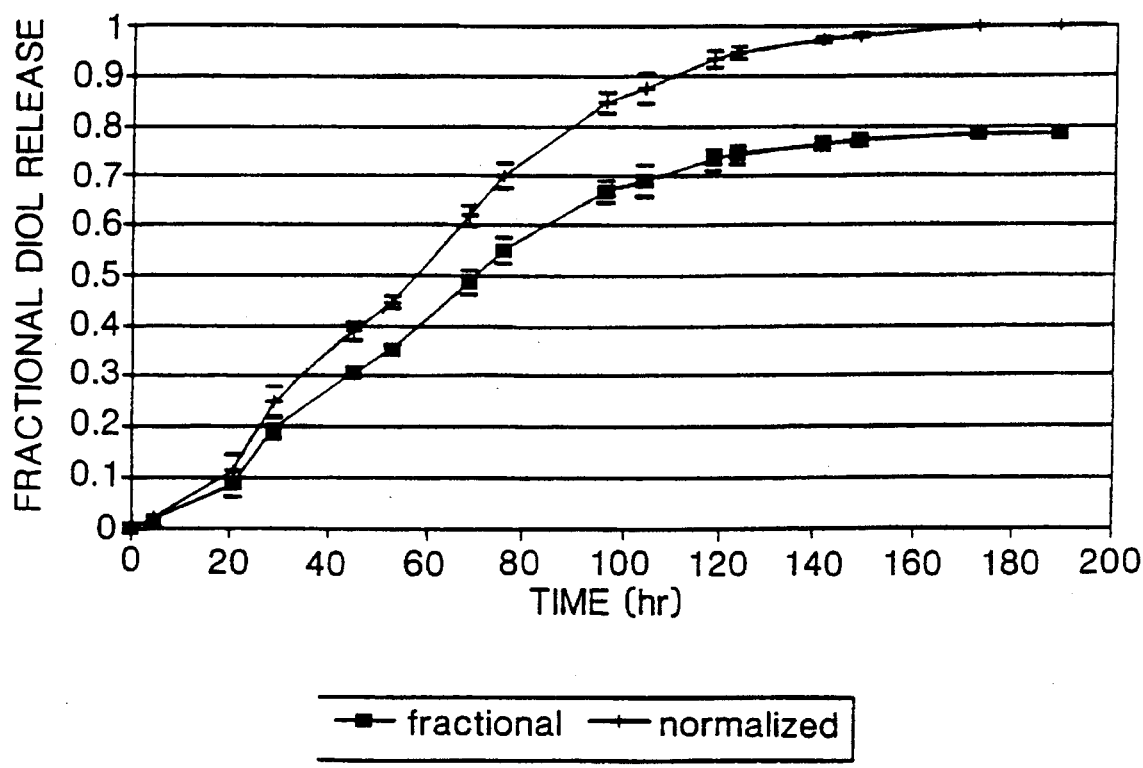
FIGS. 1a, 1b and 1c illustrate graphically the rate of erosion of a polymer/weak base single phase composition of the present invention (FIG. 1a) in comparison with a polymer/weak base two-phase composition (FIG. 1b) and the polymer alone (FIG. 1c).

Erosion rate modifiers in accordance with this invention are selected in accordance with the bioerodible polymer with which they are intended for use. The selected modifiers are those which form a solution with the polymer, and are used in amounts which permit the entire amount of modifier to be dissolved in the polymer. The modifier and polymer thus form a solid or semi-solid solution, thereby forming a single phase, with molecules of the modifier dispersed substantially uniformly and randomly throughout the continuum of the polymer, as opposed to a two-phase solid in which granules or globules of one are dispersed through, or suspended in, the other.

It is not necessary that the modifier be soluble in the polymer in all proportions. The upper solubility limit or saturation point may indeed vary widely and is not critical. In most applications, however, combinations in which the upper solubility limit of the modifier in the polymer is at least about 1.0% by weight will provide the best results. Preferred combinations are those in which the upper solubility limit is at least about 3.0% by weight, and most preferred are those in which the upper solubility limit is at least about 6.0% by weight.

Conversely, the solubility of the modifier in water is substantially lower than in the polymer. In preferred systems, the modifier is substantially insoluble in water. By "substantially insoluble in water", as used herein, is meant that the upper solubility limit in water is at most about 0.5% by weight, and in particularly preferred systems, it is at most about 0.1% by weight.

For applications of the invention in which the polymer retains a drug or other beneficial agent for slow release, preferred erosion rate modifiers are those which have a significantly lower solubility in the drug than in the polymer. Preferred systems here as well are those in which the upper solubility limit of the modifier in the drug is at most about 0.5% by weight, and in particularly preferred systems, at most about 0.1% by weight.

The selection of appropriate modifiers for any given polymer, in terms of the solubility characteristics, is achieved by routine and conventional methods. As is well known among those skilled in physical chemistry and the chemistry of solutions, the solubility of one species in another can be predicted without experiment from a knowledge of the solubility parameters of the two species. Published data on solubility parameters exists for a wide range of compounds, and further data can be readily determined by known methods. It is known that the closer the solubility parameters of two substances are to each other, the greater the mutual solubility. Determinations of appropriate modifiers for any given polymer are then a direct consequence of the knowledge of their solubility parameters.

Certain erosion rate modifiers may also serve as drugs or other beneficial agents in themselves in the same or similar types of sustained release delivery systems. The concentrations in which they are present when used as erosion rate modifiers in accordance with this invention, however, are in general considerably lower than those in which they are present when used as drugs. One surprising aspect of the invention, in fact, is that these agents have utility in the polymer matrix at concentrations so much lower than those in which they have been used as drugs. With this in mind, however, the concentration used for purposes of erosion rate modification is not critical and may vary widely. In most cases, best results will be achieved at concentrations ranging from about 0.5% to about 15% by weight, based on the polymer/modifier combination. Preferred concentrations are from about 1% to about 10% by weight.

The solid or semi-solid solution of the erosion rate modifier in the polymer may be formed by any conventional method. In general, the most efficient methods involve combining the modifier and polymer in liquid form, mixing thoroughly to achieve homogeneity, and then solidifying, preferably while forming the solidified solution into the desired ultimate shape. The components may be placed in liquid form by melting or by dissolving in solvents, then rendered solid at the appropriate stage by cooling or by solvent removal, as appropriate.

In certain cases, a pore-forming excipient is used during the formation of the polymer to form the polymer into a porous structure. In such cases, the excipient will generally be included in the liquid mixture as well. Pore-forming excipients and their use in forming porous polymer structures are well known in the art. When a pore-forming excipient of this nature is used, the erosion rate modifier is preferably one which has a greater solubility in the polymer than in the pore-forming excipient.

As indicated above, the invention permits the use of modifiers of moderate strength, since it extracts greater benefits from any given amount of modifier. In cases where the modifier is an acid or base, weak acids or bases may be used. In preferred embodiments, the acid or base will be one having a pK of at least about 2.0. For modifiers which are bases, in preferred embodiments the $pK_b$ ranges from about 4.0 to about 10.0. Likewise, for modifiers which are acids, the $pK_a$ in preferred embodiments ranges from about 4.0 to about 10.0.

Bioerodible polymers to which this invention is applicable vary widely. Certain classes of bioerodible polymers are preferred, however. One such class is that of the bioerodible poly(orthoester)s and poly(orthocarbonate)s referred to above. A particular subclass of these polymers is represented by Formula I below:

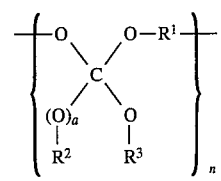

In the class defined by this formula:

The substituent $R^1$ is a divalent aliphatic or alicyclic radical.

The substituents $R^2$ and $R^3$ either: (a) are both monovalent radicals, not connected other than through the linkage shown in the formula, and are the same or different, or (b) together form a single divalent radical, thereby forming a heterocyclic ring with the two lower O atoms and the C atom shown in the formula. Whether monovalent or divalent, i.e., whether taken individually or combined, the two groups are either aliphatic, alicyclic or aromatic radicals, or radicals which are combinations of these types, or radicals of these types which further contain carbonyl or carbonyloxy groups.

As indicated above, the index "a" is zero or 1. When "a" is zero, the polymer is a poly(orthoester), and when "a" is 1, the polymer is a poly(orthocarbonate).

Finally, the index "n" is a positive integer in excess of 3, and usually in excess of 10, indicating the length of the polymer chain.

Various subclasses of ethers within the scope of Formula I are preferred. For example, preferred groups for $R^2$ and $R^3$, whether monovalent or divalent, are aliphatic, alicyclic or aromatic radicals, or radicals which are combinations of two or all three of these types. In a further preferred subclass, $R^2$ and $R^3$, whether monovalent or divalent, are aliphatic or alicyclic. In a still further preferred subclass, $R^2$ and $R^3$ when monovalent are aliphatic or alicyclic and when divalent form an aliphatic group, preferably saturated, and most preferably linear. As for $R^1$, preferred groups are divalent aliphatic and alicyclic groups, the aliphatic groups being preferably alkyl groups.

In further ways of characterizing the preferred subclasses, $R^1$ is preferably 2 to 12 carbon atoms, and most preferably 4 to 10 carbon atoms. Likewise, monovalent options for $R^2$ and $R^3$ are preferably 2 to 12 carbon atoms each, whereas divalent options are preferably 2 to 12 carbon atoms, more preferably 2 to 6 carbon atoms, and most preferably 3 to 4 carbon atoms.

The index "n" may be characterized by its value as it is above, or it may be characterized in terms of the molecular weight of the resulting polymer. In terms of molecular weight, "n" is preferably of a value which would provide the polymer with a molecular weight of at least about 1,000, and most preferably within a range of from about 1,000 to about 100,000.

Formula II below represents one preferred subclass of poly(orthoester)s:

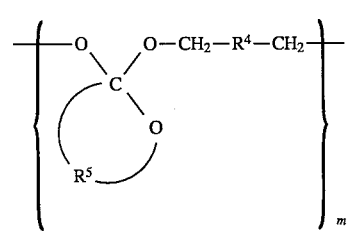

In this subclass, $R^4$ is either divalent cyclohexyl or divalent $C_1$-$C_{10}$ alkyl, and $R^5$ is either —$(CH_2)_2$—, —$(CH_2)_3$—, —(CH$_2$)$_4$— or —(CH$_2$)$_5$—. The index "m" is the counterpart to the index "n" in Formula I above, and has the same meaning and preferred ranges.

A still further subclass of poly(orthoester)s is that shown in Formula III:

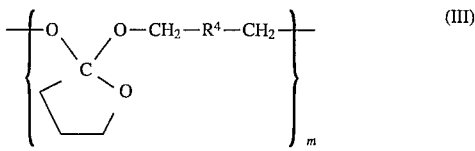

In this subclass, R$^4$ is either divalent cyclohexyl or divalent C$_3$-C$_7$ alkyl. Here again, the index "m" has the same meaning and range as "n" described earlier.

Two particularly preferred poly(orthoester)s, which fall under Formula III above, are poly(2,2-dioxy-1,6-hexamethylene tetrahydrofuran) and poly(2,2-dioxy-cis, trans-1,4-cyclohexane dimethylene tetrahydrofuran), each of which polymer has a molecular weight of from about 1,000 to about 100,000. A typical molecular weight of these polymers is 27,000.

A further preferred class of bioerodible polymers is the class consisting of polymers and copolymers of hydroxycarboxylic acids. Examples of these are polymers of d-lactic acid, polymers of l-lactic acid, polymers of d,l-lactic acid, polymers of glycolic acid, polymers of methyl ethyl glycolic acid, copolymers of lactic and glycolic acids, copolymers of caprolactone and lactic acids, and mixtures thereof. Within this class, copolymers of d,l-lactic and glycolic acids, conveniently referred to as poly(lactic/glycolic acid), are particularly preferred.

Still further bioerodible polymers for use in this invention are poly-beta-hydroxybutyrate, poly-beta-hydroxyvalerate, poly-beta-hydroxybutyrate-beta-hydroxyvalerate, polycaprolactams and polyanhydrides.

Although a wide range of erosion rate modifiers can be used, certain modifiers have been found to be particularly effective in certain polymer systems. For systems in which the polymer is poly(2,2-dioxy-cis, trans-1,4-cyclohexane dimethylene tetrahydrofuran, for example, lowering of the hydrolytic degradation rate can be achieved by the incorporation of a weak base which meets the parameters of this invention, while acceleration of the hydrolytic degradation rate can be achieved by the incorporation of a weak acid. This is also true of systems in which the polymer is poly(2,2-dioxy-1,6-hexamethylene tetrahydrofuran), as well as other poly(orthoester)s and poly(orthocarbonate)s of similar or analogous structure.

One example of a weak base which is soluble in the poly(orthoester) and not in aqueous media is bupivacaine, otherwise known as dl-1-butyl-2,6t-pipecoloxylidide. It should be noted that bupivacaine is itself useful as a local anesthetic and may thereby serve as a beneficial agent to be retained by the polymer for sustained release. When used as a beneficial agent, however, the loading of bupivacaine in the polymer (i.e., its proportion relative to the polymer) is generally at a level well in excess of its saturation level, leaving a substantial portion of the bupivacaine undissolved in the polymer. This is in contrast to its use as a degradation rate regulator, in which the loading is at or below the saturation level.

One example of a weak acid for use with the poly(orthoester) is benzoic acid.

For systems in which the polymer is a polymer of d,l-lactic acid, a polymer of glycolic acid, a mixture of the two, or a copolymer of d,l-lactic and glycolic acids, both a weak base and a weak acid will have the effect of accelerating the rate of hydrolytic degradation. Bupivacaine and benzoic acids are again examples of a weak base and a weak acid which will have this effect.

The compositions of the present invention may additionally include, if desired, one or more diluents, surfactants, buffers, vehicles, stabilizers, dyes, inert fillers, pigments and other components of polymeric matrix systems as are known in the art.

In certain cases, a hydrophilic pore-forming excipient is used during the formation of the polymer to form the polymer into a porous structure. Such excipients may be chosen from a wide range of materials. Examples are alkali metal salts such as sodium chloride and potassium chloride; monosaccharides, oligosaccharides and polysaccharides, notably sucrose, glucose, fructose and trehalose; polyalcohols such as mannitol and sorbitol; and water-soluble cellulosic polymers such as methyl cellulose and hydroxypropylmethyl-cellulose.

Other excipients are optionally included. One class of such excipients are inert hydrophobic excipients that act to increase drug delivery and improve reproducibility from certain polymers. Examples of this type of excipient are calcium stearate, magnesium stearate, aluminum stearate, calcium phosphate, myciyl cerotate, β-carotene, zeaxanthin, cholestane, 3-hydroxycholestane, cholesterol, 5,6-cholestene, 3-hydroxy-5,6-cholestene, and 3-amino-5,6-cholestene.

As indicated above, the invention is of particular interest in sustained-release drug delivery formulations in which the drug is incorporated in the polymer matrix together with the erosion rate modifier. Incorporation of the drug into the polymer/modifier matrix may be achieved in any of the various ways described in the prior art. A prominent example is to combine the drug with the polymer and modifier in a liquid form to achieve the appropriate weight ratio and consistency, and then to solidify the combined polymer and drug while forming the combination into the desired size and shape. The drug is typically present in the polymer in a therapeutically effective amount, by which is meant an amount that is necessary to effect a therapeutic result. In practice, the particular amount will vary widely, depending on many factors, such as the drug to be delivered, the therapeutic effect desired, the chosen environment of use, the rate of delivery, the length of treatment, and the like.

The term "drug" is used in this specification in a broad, generic sense, to include any physiologically or pharmacologically active substances that produce a localized or systemic effect or effects in animals. Examples of drugs will be readily apparent to those skilled in the art. Therapeutic agents or drugs with which the polymers of the present invention are particularly useful are those agents which are sensitive to acids or bases, such as, for example, proteins and peptides.

In the practice of the present invention, the delivery devices of the invention are placed in or on an aqueous environment of use. The environments in which the devices may be used include physiological environments within the body of a human or animal or aqueous environments such as pools, tanks, reservoirs, and the like serving recreational, industrial or residential purposes. The devices may also be utilized in the biotechnology area, such as to deliver nutrients or growth regulating compounds or other agents to cell cultures, for example. In the presently preferred embodiments, the environment of use is the body of an animal. Included in the term "animal" are humans, primates, mammals, domesticated or semi-domesticated animals (such as household, pet, and farm animals), laboratory animals (such as mice, rats and guinea pigs), birds, reptiles, fish, zoo animals, and the like. The devices may be placed on or in wounds, spread as a thin film, or injected as microparticles or placed subcutaneously or interperitoneally as an implant into the body, for example.

The delivery devices of the present invention can take a variety of shapes and sizes, such as sheets, films, rods, fibers, monofilaments, pellets, spheres and spheroids, particles and microparticles, powders, tubes, discs, rings, and the like, depending on the use to which they will be applied. The devices can be sized, shaped and adapted for implantation, insertion, placement, depositing or spreading on the body, in the body, or in cavities and passageways of the body of an animal. The devices can be manufactured by standard techniques known to the art.

The following examples are offered for purposes of illustration, and are intended neither to limit nore to define the invention in any manner.

EXAMPLE 1

A comparison was conducted, as follows, of the degradation rate of a polymer/weak base matrix of the present invention with that of the polymer without a base additive and of the polymer together with the weak base where the base is in a separate phase.

The polymer/base matrix of the invention was prepared by mixing together, at 120° C., bupivacaine base (5%) and the poly(orthoester) of Formula IV (above), having a molecular weight of about 30,000, until the two components were well blended. The resulting single-phase blend was melt-pressed into a sheet of 0.25 mm thickness. The sheet was then cut into 1 cm×1 cm squares. All the processing was carried out under dry nitrogen gas. The squares were packaged in double foil pouches and irradiated, receiving a dose of 2.5 Mrad of beta radiation.

A polymer/base matrix according to the prior art was prepared by mixing together, at 60° C., bupivacaine base (5%) and the poly(orthoester) of Formula IV, having a molecular weight of about 30,000, until the two components were well mixed. The resulting two-phase mixture was then formed into squares and irradiated following the procedures described above.

The poly(orthoester) alone was heated to 60° C. and formed into squares and irradiated following the above procedures.

Figure 1B:
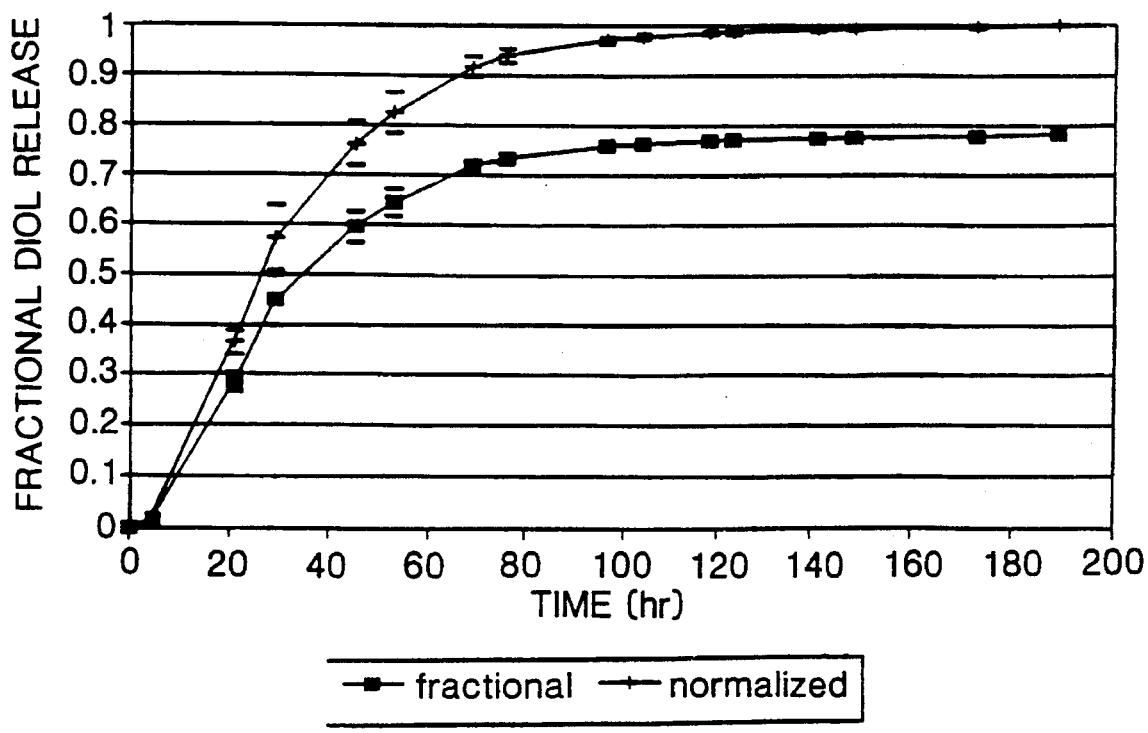
Figure 1C:
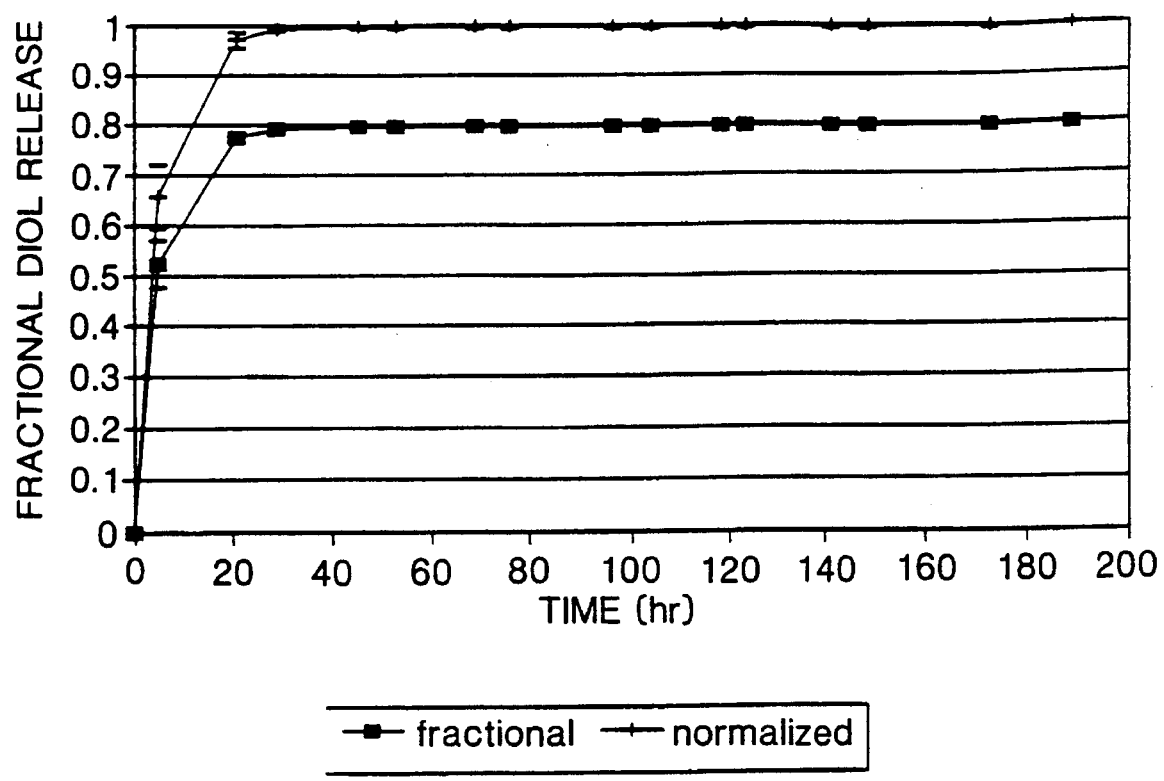

A degradation rate experiment was conducted on samples from each of the above systems by placing the irradiated systems in 5 mL of pH 7 0.01M sodium phosphate buffer (which also contained 0.9% of NaCl and 0.02% $NAN_3$). Samples of the release rate media were taken each day and tested for presence of cyclohexanedimethanol. The release of cyclohexanedimethanol (diol) is an indication of polymer erosion. The resulting diol release for each system is presented in FIG. 1a (polymer/bupivacaine single-phase blend), FIG. 1b (polymer/bupivacaine two-phase mixture), and FIG. 1c (polymer alone). The systems having the bupivacaine and polymer together in a single-phase showed a markedly slower rate of erosion than either the polymer/bupivacaine two-phase mixture or the polymer alone.

EXAMPLE 2

A comparison was made as follows of the degradation rate of a polymer/weak organic base matrix of the present invention with that of a polymer/strong inorganic base matrix of the prior art.

Inorganic bases generally can achieve higher pH values than organic bases, and thus are considered to be stronger bases. For example, a saturated solution of dibasic potassium phosphate has a pH of 11 whereas a saturated solution of bupivacaine base has a pH below 9. This is a 100+ fold difference in concentration of hydroxyl ions.

A composition of poly(orthoester) and bupivacaine base, formed as a single phase, was prepared by mixing together, at a temperature of 120° C, bupivacaine base (8%) and the poly(orthoester) of Formula IV (above; 92%), having a molecular weight of about 30,000. Part of this single-phase blend (650 mg) was then mixed at 60° C. with lysozyme (a protein; 50 mg), trehalose (150 mg), pH 7 potassium phosphate buffer (25 mg of dibasic potassium phosphate and 25 mg of potassium dihydrogenphosphate), and cholesterol (100 mg). The lysozyme and trehalose had been previously co-lyophilized. All the ingredients, except the polymer/bupivacaine mix, were micronized to 5 microns and dried to a water content of less than 0.1% prior to mixing. The resulting mixture was melt-pressed into a sheet of 0.25 mm thickness. The sheet was then cut into 1 cm×1 cm squares. All the processing was carried out under dry nitrogen gas. The squares were packaged in double foil pouches and irradiated, receiving a dose of 2.5 Mrad of beta radiation.

A composition of poly(orthoester) and dibasic potassium hydrogenphosphate, as a mixture together with lysozyme, was prepared by mixing together lysozyme (100 mg), dibasic potassium phosphate (50 mg), cholesterol (150 mg) and the poly(orthoester) of Formula IV (700 mg) in a mixer heated at 60° C. for 10 minutes. The lysozyme, dibasic potassium phosphate and cholesterol were previously micronized to a particle size of 5 microns and dried to a water content of less than 0.1%. The resulting polymer/base/lysozyme mixture was then formed into squares and irradiated following the procedures described above.

Figure 2A:
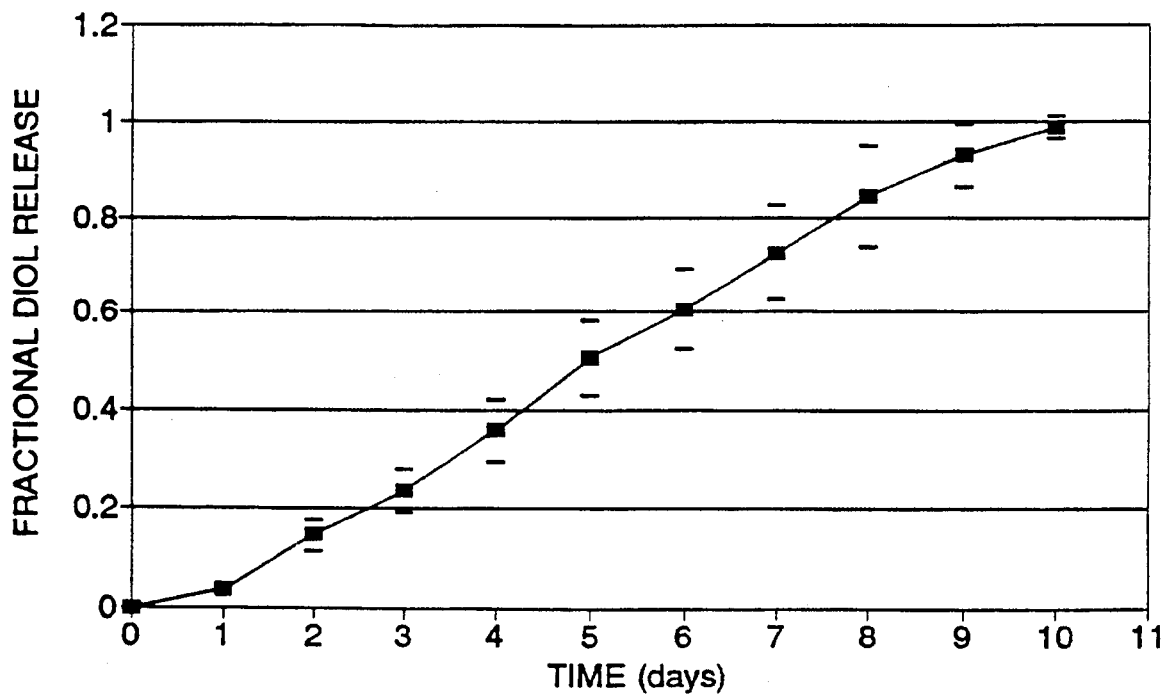
FIGS. 2a and 2b illustrate graphically the rate of erosion of a polymer/weak base single phase composition of the present invention (FIG. 2a) and of a polymer/strong base two-phase composition (FIG. 2b).
Figure 2B:
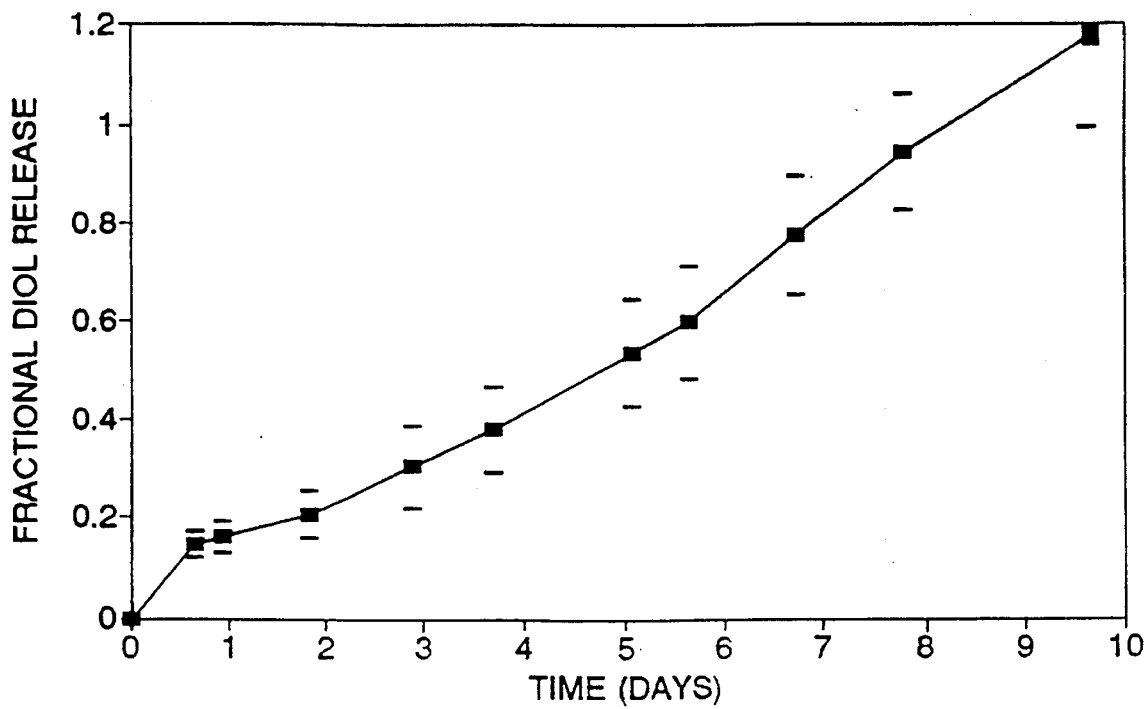

A degradation rate experiment was conducted on samples from each of the above systems by placing the irradiated systems in 5 mL (polymer/bupivacaine single-phase system) or 10 mL (polymer/dibasic potassium phosphate two-phase system) of pH 7 0.01M sodium phosphate buffer (which also contained 0.9% of NaCl and 0.02M $NaN_3$). Samples of the release rate media were taken each day and tested for presence of cyclohexanedimethanol. The release of cyclohexanedimethanol (diol) is an indication of polymer erosion. The resulting diol release for each system is presented in FIGS. 2a (polymer/bupivacaine single-phase system) and 2b (polymer/dibasic potassium phosphate two-phase system). The erosion of the systems containing bupivacaine was of approximately the same degree of slowness as that of the system with dibasic potassium phosphate, even though bupivacaine is a much weaker base than dibasic potassium phosphate.

EXAMPLE 3

PLGA [poly(lactic-glycolic acid), 50:50 lactic:glycolic acids, Resomer® RG 503, Boehringer Ingelheim] was mixed with 10% (w/w) of either benzoic acid or pyruvic acid. The mixing was done in a 1.5 cc mechanical polymer mixer, in both cases at temperatures above the melting point of the acid to give single-phase blends. The mixing temperature was initially around 140° C., and was subsequently lowered as the mixed-in acids plasticized the polymer. In both cases, clear mixtures were obtained.

The intention of mixing acids in PLGA is to increase the degradation rate of the polymer. The degradation rates of the two polymer blends and of neat PLGA were compared.

Benzoic acid, having a very low solubility in water at 37° C., was retained well in the PLGA and was an effective degradation rate enhancer. After 4 weeks in a phosphate buffered physiological saline solution at 37° C., neat PLGA was about 60% degraded, while the PLGA with benzoic acid was more than 90% gone. In contrast, pyruvic acid, being highly water soluble, was rapidly lost to the release medium, and accelerated the degradation much less efficiently. The polymer with the pyruvic acid initially degraded more rapidly than the neat PLGA, but over time its degradation rate accelerated less than that of the neat PLGA, and after 4 weeks about 65% of the PLGA with pyruvic acid was degraded.

The foregoing is offered primarily for purposes of illustration. It will be readily apparent to those skilled in the art that the materials, proportions, operating conditions, and other parameters of the systems and methods described herein may be further modified or substituted in various ways without departing from the spirit and scope of the invention.

What is claimed is:

1. A method for altering the erosion rate of a drug-containing bioerodible composition to obtain a predetermined rate of drug release therefrom, said composition comprising a polymer selected from the group consisting of polymers and copolymers of d,l-lactic and glycolic acids and mixtures thereof, said method comprising:

a) forming a dispersion of said drug in said polymer; and b) completely dissolving in said dispersion so that a single homogenous phase is formed an amount of an erosion rate modifier sufficient to produce an erosion rate of said composition that is different than the erosion rate of the composition in the absence of said modifier, said erosion rate modifier being selected from the group consisting of weak acids and bases which are soluble in said polymer, substantially insoluble in water and have a pK of at least about 2.0.

2. A method in accordance with claim 1 wherein said erosion rate modifier is a base having a $pK_b$ of from about 4.0 to about 10.0.

3. A method in accordance with claim 1 wherein said erosion rate modifier is an acid having a $pK_a$ of from about 4.0 to about 10.0.

4. A method in accordance with claim 2 wherein said base is bupivacaine base.

5. A delivery device for the controlled administration of a beneficial agent to an environment of use, wherein the device comprises:

(a) a shaped matrix sized and adapted for administering a drug to an animal, said matrix comprising a bioerodible polymer wherein said polymer is a member selected from the group consisting of polymers and copolymers of d,l-lactic and glycolic acids and mixtures thereof and a predetermined amount of an erosion rate modifier sufficient to produce an erosion rate of the matrix that is different from that of a matrix without the erosion rate modifier, the erosion rate modifier selected from an acid or a base which is soluble in said polymer and substantially insoluble in water and has a pK of at least 2.0, said erosion rate modifier being dissolved in said bioerodible polymer, said erosion rate modifier and said polymer forming a single homogeneous phase; and (b) the beneficial agent to be delivered, dispersed in said matrix in a therapeutically effective amount.

6. A delivery device in accordance with claim 5 in which said erosion rate modifier is a base having a $pK_b$ of from about 4.0 to about 10.0.

7. A delivery device in accordance with claim 5 in which said erosion rate modifier is an acid having a $pK_a$ of from about 4.0 to about 10.0.

8. A delivery device in accordance with claim 5 wherein said erosion rate modifier is selected from the group consisting of bupivacaine base and benzoic acid.

9. A method in accordance with claim 1 wherein steps a) and b) are performed simultaneously.

10. A delivery device in accordance with claim 5 wherein said beneficial agent is bupivacaine.

* * * * *